US011712268B2

(12) United States Patent
Kiester

(10) Patent No.: US 11,712,268 B2
(45) Date of Patent: *Aug. 1, 2023

(54) EXPANDABLE ROD SYSTEM TO TREAT SCOLIOSIS AND METHOD OF USING THE SAME

(71) Applicant: NuVasive Specialized Orthopedics, Inc., San Diego, CA (US)

(72) Inventor: P. Douglas Kiester, Irvine, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 97 days.

This patent is subject to a terminal disclaimer.

(21) Appl. No.: 17/227,291

(22) Filed: Apr. 10, 2021

(65) Prior Publication Data
US 2021/0228242 A1 Jul. 29, 2021

Related U.S. Application Data

(60) Continuation of application No. 16/003,606, filed on Jun. 8, 2018, now Pat. No. 11,357,549, which is a
(Continued)

(51) Int. Cl.
*A61B 17/70* (2006.01)
*A61B 17/68* (2006.01)

(52) U.S. Cl.
CPC .......... *A61B 17/7016* (2013.01); *A61B 17/70* (2013.01); *A61B 17/7004* (2013.01); *A61B 17/7023* (2013.01); *A61B 2017/681* (2013.01)

(58) Field of Classification Search
CPC ................ A61B 17/70; A61B 17/7004; A61B 17/7014–7017; A61B 17/7023
See application file for complete search history.

(56) References Cited

U.S. PATENT DOCUMENTS 2,702,031 A 2/1955 Wenger
3,111,945 A 11/1963 Von Solbrig
(Continued)

FOREIGN PATENT DOCUMENTS

CN 1697630 A 11/2005
CN 101040807 A 9/2007
(Continued)

OTHER PUBLICATIONS

Abe et al., "Experimental external fixation combined with percutaneous discectomy in the management of scoliosis.", Spine, 1999, pp. 646-653, 24, No. 7.
(Continued)

*Primary Examiner* — Nicholas J Plionis
(74) *Attorney, Agent, or Firm* — Hoffman Warnick LLC

(57) ABSTRACT

Correction of a scoliotic curve in a spine comprises the steps of implanting an expanding rod isolated completely under the skin and attached to selected portions of the scoliotic curve of the spine at opposing ends of the rod; and producing a controlled force by means of expansion of the rod over at an extended time period under externa control until a desire spinal curve is obtained. An incremental force is generated to stretch the scoliotic curve of the spine between the selected portions where attachment of the rod is defined. The controlled force is provided steadily for at least one month or alternatively 1-3 months. Multiple rods may be employed each associated with a different scoliotic curve of the spine or a different portion of the scoliotic curve.

17 Claims, 6 Drawing Sheets

Related U.S. Application Data continuation of application No. 15/192,917, filed on Jun. 24, 2016, now Pat. No. 10,016,221, which is a continuation of application No. 14/321,386, filed on Jul. 1, 2014, now Pat. No. 9,398,925, which is a continuation of application No. 13/691,530, filed on Nov. 30, 2012, now Pat. No. 8,852,236, which is a continuation of application No. 12/421,569, filed on Apr. 9, 2009, now Pat. No. 8,343,192, which is a division of application No. 11/172,678, filed on Jun. 30, 2005, now Pat. No. 7,955,357.

(60) Provisional application No. 60/584,961, filed on Jul. 2, 2004.

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A * | 8/1976 | Hildebrandt ....... A61B 17/8004 606/241 |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,445,513 A | 5/1984 | Ulrich et al. |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A * | 11/1996 | Chen ................. A61B 17/7014 606/264 |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,200,324 B1 | 3/2001 | Regni, Jr. |
| 6,234,956 B1 | 5/2001 | He et al. |
| 6,241,730 B1 | 6/2001 | Alby |
| 6,245,071 B1 | 6/2001 | Pierson |
| 6,245,075 B1 | 6/2001 | Betz et al. |
| 6,251,111 B1 * | 6/2001 | Barker ............... A61B 17/7041 606/86 A |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |

(56) References Cited

U.S. PATENT DOCUMENTS

| | | |
|---|---|---|
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,481,841 B2 | 1/2009 | Hazebrouck et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,942,908 B2 | 5/2011 | Sacher et al. |
| 7,955,357 B2 | 6/2011 | Kiester |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Amin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,343,192 B2 | 1/2013 | Kiester |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |

(56) References Cited

U.S. PATENT DOCUMENTS

| | | |
|---|---|---|
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,623,092 B2 | 1/2014 | Bickley et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van Den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,852,236 B2 | 10/2014 | Kiester |
| 8,870,881 B2 | 10/2014 | Rezach et al. |
| 8,870,959 B2 | 10/2014 | Amin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,398,925 B2 | 7/2016 | Kiester |
| 10,016,221 B2 | 7/2018 | Kiester |
| 2002/0050112 A1 | 5/2002 | Koch et al. |
| 2002/0072758 A1 | 6/2002 | Reo et al. |
| 2002/0138077 A1* | 9/2002 | Ferree ............... A61B 17/7014 606/259 |
| 2002/0151978 A1 | 10/2002 | Zacouto et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0030395 A1* | 2/2004 | Blunn ............... A61B 17/7016 623/23.45 |
| 2004/0055610 A1 | 3/2004 | Forsell |
| 2004/0133219 A1 | 7/2004 | Forsell |
| 2004/0138663 A1 | 7/2004 | Kosashvili et al. |
| 2004/0138725 A1 | 7/2004 | Forsell |
| 2004/0193266 A1 | 9/2004 | Meyer |
| 2004/0215191 A1 | 10/2004 | Kitchen |
| 2004/0236329 A1 | 11/2004 | Panjabi |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0107787 A1 | 5/2005 | Kutsenko |
| 2005/0113927 A1 | 5/2005 | Malek |
| 2005/0159754 A1 | 7/2005 | Odrich |
| 2005/0203517 A1 | 9/2005 | Jahng et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2005/0277932 A1 | 12/2005 | Farris |
| 2006/0004447 A1 | 1/2006 | Mastrorio et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0055125 A1 | 3/2007 | Anderson et al. |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0213812 A1 | 9/2007 | Webler et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Coumoyer et al. |
| 2008/0033431 A1 | 2/2008 | Jung et al. |
| 2008/0033436 A1 | 2/2008 | Song et al. |

(56) References Cited

U.S. PATENT DOCUMENTS

| | | |
|---|---|---|
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0204156 A1 | 8/2009 | McClintock et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0049204 A1 | 2/2010 | Soubeiran |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0217271 A1 | 8/2010 | Pool et al. |
| 2010/0228167 A1 | 9/2010 | Ilovich et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0137347 A1 | 6/2011 | Hunziker |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0022597 A1 | 1/2012 | Gephart et al. |
| 2012/0053633 A1 | 3/2012 | Stauch |
| 2012/0088953 A1 | 4/2012 | King |
| 2012/0089191 A1 | 4/2012 | Altarac et al. |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | 2004019796 A1 | 3/2004 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection,", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

(56) References Cited

OTHER PUBLICATIONS

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children,", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening,", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy,", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding,", Obesity Surgery, 2002, pp. 285-288, 12, No. 2.

Fried et al., "In vivo measurements of different gastric band pressures towards the gastric wall at the stoma region,", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing,", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD),", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral malrotation following intramedullary nailing of the femur,", Acta Orthop Belg, 2010, pp. 580-584, 76, No. 5.

Klemme et al., "Spinal instnimentation without fusion for progressive scoliosis in young children", Journal of Pediatric Orthopaedics. 1997, pp. 734-742, 17, No. 6.

Korenkov et al., "Port function after laparoscopic adjustable gastric banding for morbid obesity.", Surgical Endoscopy, 2003, pp. 1068-1071, 17, No. 7.

Krieg et al., "Leg lengthening with a motorized nail in adolescents.", Clinical Orthopaedics and Related Research, 2008, pp. 189-197, 466, No. 1.

(56) References Cited

OTHER PUBLICATIONS

Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering-General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?.", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrmmentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu vamm deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany, (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013, Vancouver, Canada. Scoliosis Research Society.
Sun et al., "Masticatory mechanics of a mandibular distraction osteogenesis site: Interfragmentary micromovement", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Hamngton instmmentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.

(56) References Cited

OTHER PUBLICATIONS

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

* cited by examiner

EXPANDABLE ROD SYSTEM TO TREAT SCOLIOSIS AND METHOD OF USING THE SAME

RELATED APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The invention relates to the field of medical devices for treating scoliosis and methods of treatment using such medical devices, or methods of using such devices.

Description of the Prior Art

Adolescent (also called idiopathic) scoliosis is believed to be the direct result of a tight ligamentum flavum during rapid growth. The ligamentum flavum is a strong discontinuous (or segmental) ligament full of elastic fibers (which gives it its yellow color) that runs along the posterior aspect of the spinal canal. The posterior aspect of the dura, at any given spinal level, touches lamina for one third of its length, and ligamentum for the other two thirds. In the lumbar spine it acts as the center of rotation (and may be the center of rotation for the thoracic as well, which would help explain the limited rotation available in the thoracic spine).

If Indeed scoliosis is the result of a tight ligamentum flavum, then correction of scoliosis should be achievable by mechanical stretching. Rapid correction of a scoliotic curve is now possible because great force through multiple points of solid fixation are now available. These methods still, however, are described as steps toward inserting instrumentation for a fusion of vertebrae. A slower and steady stretch over time, would be much less violent, and would allow the use of much less force and fewer points of fixation.

What is needed is some kind of device and mechanics to perform the needed mechanical stretching.

BRIEF SUMMARY OF THE INVENTION

The Illustrated embodiment of the invention includes a method for correction of a scoliotic curve in a spine comprising the steps of implanting an expanding rod isolated completely under the skin and attached to selected portions of the scoliotic curve of the spine at opposing ends of the rod; and producing a controlled force by means of expansion of the rod over at an extended time period under external control until a desire spinal curve is obtained.

The step of producing a controlled force comprises the step of generating an incremental force to stretch the scoliotic curve of the spine between the selected portions where attachment of the rod is defined. The step of generating an incremental force to stretch the scoliotic curve of the spine comprises the step of generating a force using a curved rod in a direction tending to align with the spine at the selected portions where attachment of the rod is defined.

The step of implanting the expanding rod comprises implanting the expanding rod posteriorly to the spine.

The step of producing a controlled force by means of expansion of the rod over at an extended time period comprises the step of producing the controlled force at a predetermined level over time without any combination with fusion of vertebrae.

The step of producing the controlled force by means of expansion of the rod over at an extended time period comprises producing the controlled force steadily for at least one month or alternatively 1-3 months.

The step of producing the controlled force by means of expansion of the rod over at an extended time period comprises the step of producing the controlled force steadily for such period of time as is sufficient to stretch the ligamentum flavum of the spine enough to allow the spine to straighten.

The invention further contemplates repeating the steps of implanting an expanding rod with multiple rods, where each rod is associated with a different scoliotic curve of the spine or a different portion of the scoliotic curve of the spine, and separately producing a controlled force by means of expansion of each corresponding rod over at a corresponding extended time period.

The step of producing the controlled force by means of expansion of the rod comprises the step of producing the controlled force by means of a ratcheted longitudinal extension of the rod powered by an energy sources biologically isolated from the rod by a skin barrier.

The invention also comprises an apparatus used for performing each of the above embodiments of the illustrated method. The invention thus includes among other embodiments a kit of a plurality of expanding rods with multiple rods, each rod being associated with a different scoliotic curve of the spine or a different portion of the scoliotic curve of the spine and separately producing a controlled force by means of expansion of each corresponding rod over at a corresponding extended time period.

The means for producing the controlled force by means of expansion of the rod comprises means for producing the controlled force by a ratcheted longitudinal extension of the rod powered by an energy sources biologically isolated from the rod by a skin barrier.

Stated in an alternative form, the invention includes embodiments where the invention is an apparatus for correction of a scoliotic curve in a spine comprising an expanding rod isolated completely under the skin; attachment screws to couple the rod to the spine at opposing ends of the rod; and a source of controlled force coupled to the rod to longitudinal extend the rod over an extended defined period of time under external control until a desire spinal curve is obtained.

The rod comprises a pair of telescopically coupled sleeves; and means to prevent relative rotation of the sleeves. The apparatus is combined with an external source of power, and in one embodiment the source of the controlled force comprises a torsion spring coupled to a second one of the pair of sleeves, a torsion motor coupled to the spring for torsioning the torsion spring, a power pick up electrically coupled to the torsion motor for powering the motor from the external source of power, a ratchet and a screw drive coupled to the ratchet at one end and to a first one of the pair of sleeves at an opposing end, so that a force applied to the screw drive from the torsion motor to the first one of the pair of sleeves over time longitudinally expands the collective length of the pair of sleeves. In the illustrated embodiment the torsion motor comprises a muscle wire.

More generally, where the invention is characterized as a combination of an expanding rod, attachment screws, a source of controlled force, and a ratchet, where the source of controlled force produces a force over a defined period of time, which force is continually maintained to some degree by the ratchet after initial generation by the source until the spine to which the force is steadily applied straightens at least to a partial degree.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
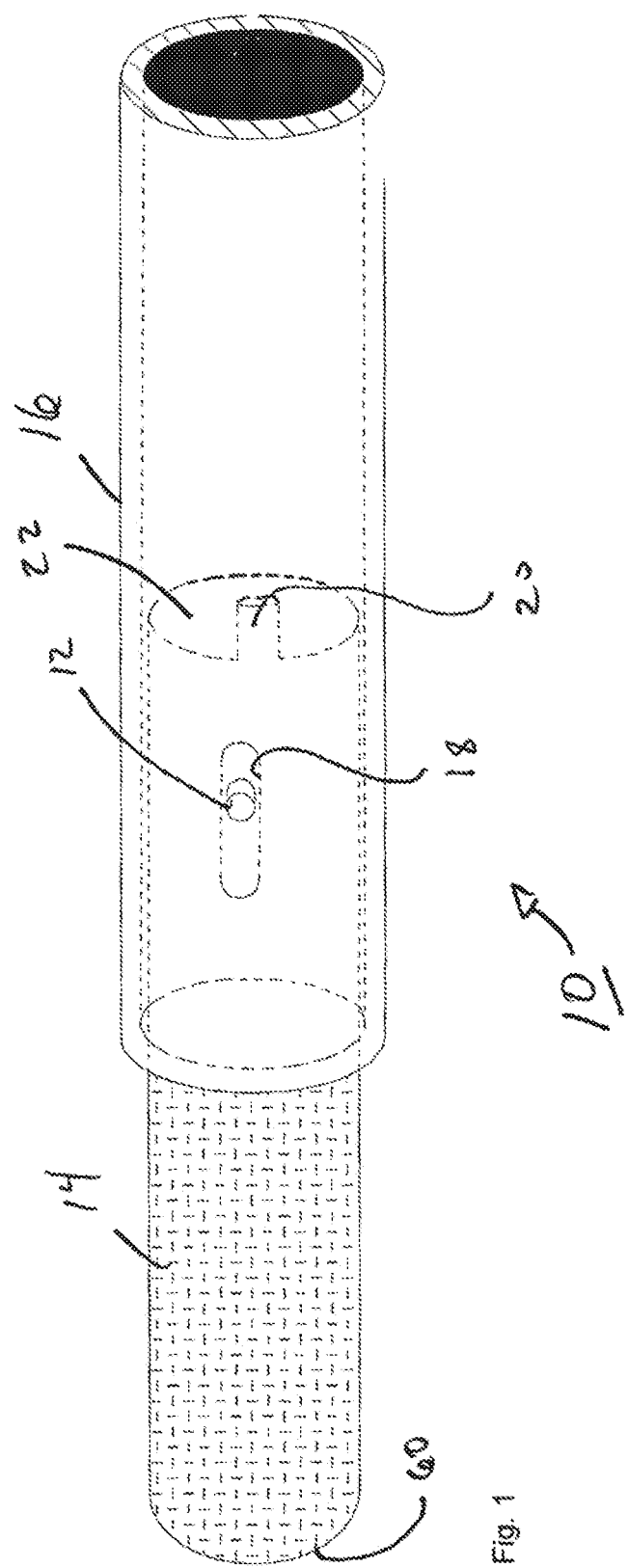
FIG. 1 is a side perspective view of a telescoping rod of the invention showing the telescopic sleeves.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The invention comprises a rod, generally denoted by reference numeral 10, for the treatment of scoliosis by slow stretching of selected biological tissues, for example, a selected portion of the spine, which is implantable into the body and is under external control. The invention allows for surgical treatment of the spine without fusion of any of the vertebrae, and can be used not only for scoliosis, but also in pediatric orthopedics such as for leg or limb lengthening.

For the purposes of the illustrated disclosure, it is assumed that adolescent (also called idiopathic) scoliosis is the direct result of a tight ligamentum flavum during rapid growth. The evidence for this assumption is impressive and overwhelming. The second assumption made in the illustrated disclosure for the sake of simplicity is that we are treating a simple, single curve, although the indications and complexities of extending the use of the invention to more complex curves is explicitly within the scope of the invention. Where multiple rods 10 are implanted each rod 10 may be fixed across a different scoliotic curve where multiple scoliotic curves exist, or may be fixed across different portions of a single scoliotic curve. In such a case, each one of the multiple rods can be separately controlled to produce the needed straightening force or expansion.

The proposed device comprises an expanding or telescopic rod 10 as shown in side perspective view in FIG. 1. As described below, the opposing ends of rod 10 will be fixed to selected positions on the spine using conventional surgical screws. The rod 10 must produce a controlled force, slowly over time, under precise external control, and be isolated or implanted completely under the skin and protected by the natural barrier, which the skin provides. Rod 10 also needs to be small, powerful, simple enough to be readily manufactured, immune to accidental activation, and biologically inert. Rod 10 of the illustrated embodiment meets each and all of these criteria.

The rod 10 can be as small as ½" (2.54 cm) in diameter and typically can be made much smaller, subject only material limitations arising from the strength of the rod 10 itself. Rod 10 is can be made from any bioengineered or biological inert material desired, and in the illustrated embodiment is fabricated from metal, such as surgical quality stainless steel. Rod 10 is comprised of an inner hollow cylindrical sleeve 14 telescopically disposed in outer, hollow cylindrical sleeve 16. The outer diameter of cylindrical sleeve 14 is chosen to telescopically slide without binding in the inner diameter of cylindrical sleeve 16 along their common longitudinal axes. A pin 12 is fixed to cylindrical sleeve 14 and extends radially therefrom through a longitudinal slot 18 defined through the wall of cylindrical sleeve 16 to stop rotation of cylindrical sleeve 14 relative to cylindrical sleeve 16 while allowing free relative longitudinal movement of cylindrical sleeve 14 relative to cylindrical sleeve 16 at least to the extent of the length of slot 18. Sleeves 14 and 16 are shown as circular cylinders in the illustrated embodiment, but pin 12 may be removed and elliptically or other prismatic shapes may be used in place of a cylindrical shape, which would equivalently stop or limit their relative rotation to each other. Therefore, when in the specification the term, "sleeve" is used without modification, it should be understood to have a general prismatic shape.

Figure 2:
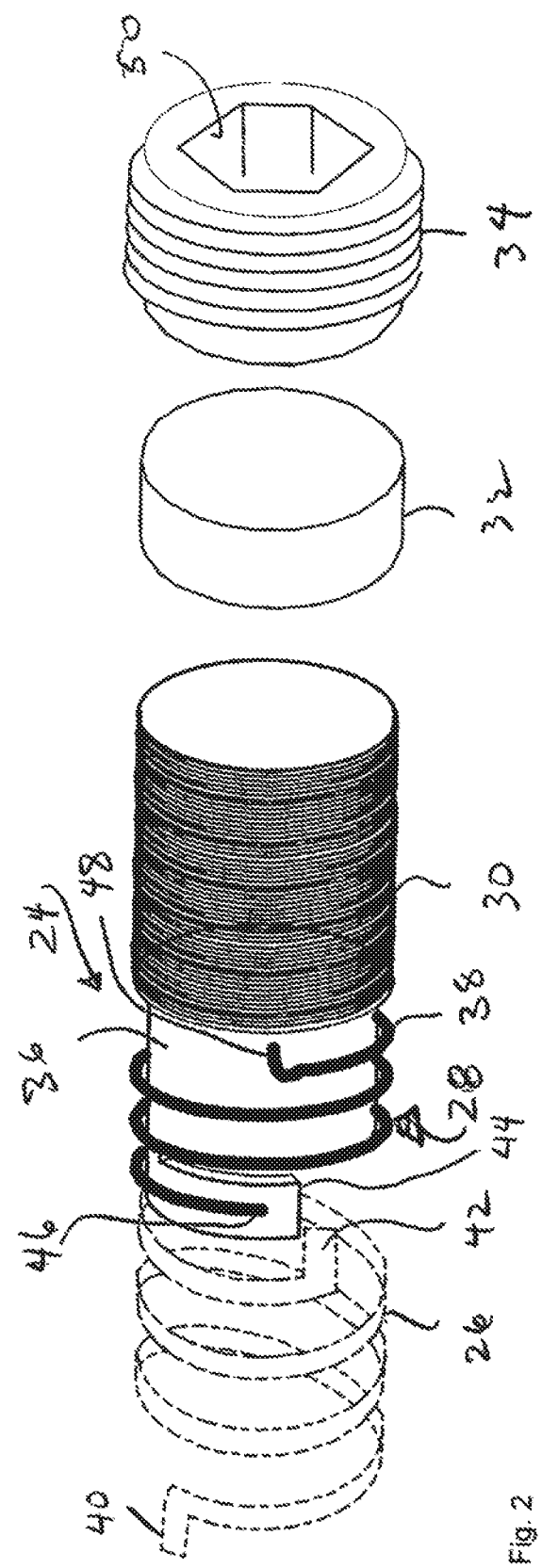
FIG. 2 is a side perspective view of a drive unit of the illustrated embodiment of the invention included in the rod of FIG. 1.
Figure 2A:
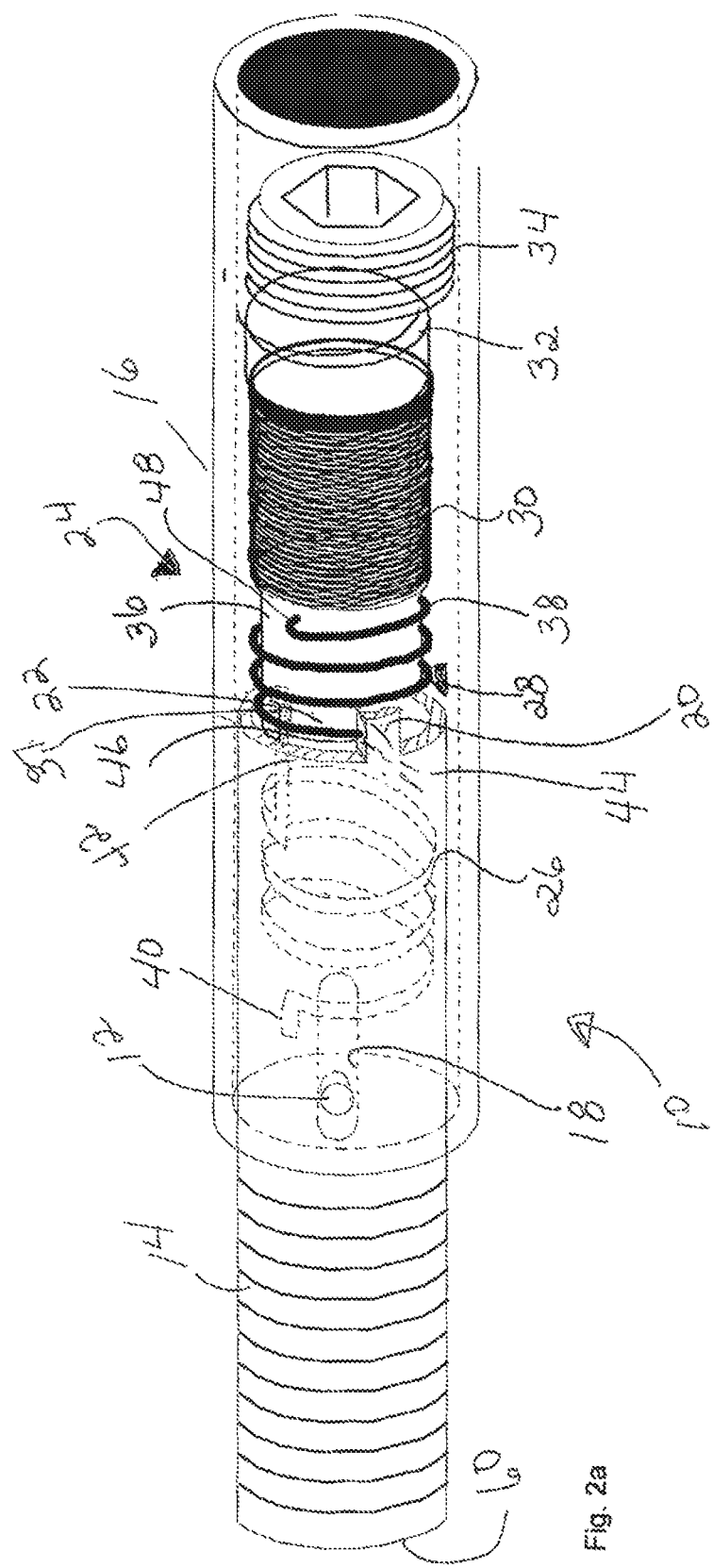
FIG. 2a is a side perspective transparent view of the invention as depicted in FIGS. 1 and 2 shown in assembled form.

The larger cylindrical sleeve 16 is internally threaded. The small longitudinally extending post 20 on the right end 22 of the smaller cylindrical sleeve 14 as seen in FIG. 1 is where the drive unit, generally denoted by reference numeral 24, attaches as described below. Drive unit 24 as shown in the side perspective view of FIG. 2 is housed or disposed inside the cylindrical sleeve 16 with the left end 40 of a torsion spring 26 disposed within and affixed to sleeve 14 as shown in FIG. 2a. The opposing end 42 of torsion spring 26 is coupled to or bears against a segment end 44 of shell 36. Shell 36 is disposed in sleeve 16 as shown in FIG. 2a and rotates within the end of sleeve 14, but is held by a stop(s) 37 from telescopically sliding into sleeve 14. Shell 36 is thus longitudinally fixed relative to sleeve 14, but is free to rotate relative to sleeve 14 at least through a defined angular range. Thus, as shell 36 is rotated as described below, torsion spring 28 which has on end connected to sleeve 14 and the other end to shell 38 will wind up or down depending on the sense of rotation of shell 36.

FIG. 2 shows the drive unit in exploded view which is comprised of spring 26, motor 28, pickup coil 30, ratchet 32 and screw drive 34. These elements represent the simplest configuration for the drive unit 24, although it must be understood that any drive unit now known or later devised capable of providing the same or similar force as the illustrated drive unit 24 can be equivalently substituted without departing from the illustrated embodiment of the invention. Because of energy transfer considerations relating to coil 30 and wire 38, additional electronic or electrical components may be required as discussed below.

The motor 28 comprises a muscle wire 38 wound onto a cylindrical shell 36. Muscle wire 38 is well known to the art and is also called nitinol wire. When current is passed through the wire 38, it heats and contracts. Wire 38 is electrically connected to or in circuit with coil 30 in which a current is inductively generated. One end 48 of wire 38 is coupled or connected to shell 38. The opposing end 48 of wire 38 is coupled or connected to sleeve 14 at post 20 as shown in FIG. 2a. The contraction of wire 38 causes the entire remaining portion of drive unit 24 to rotate against the spring 26, in other words, as wire 38 ohmically heats due to the current supplied to it from coil 30 and its length contracts, wire 38 will cause shell 36 to rotate. Shell 36 is rotationally coupled or connected to ratchet 32, which rotates with shell 36 in both senses of rotation. Ratchet 32 is coupled to screw drive 34 through a conventional ratcheting mechanism (not shown) thereby causing screw drive 34 to rotate in one sense of rotation, but slipping with respect to screw drive 34 in the opposite sense of direction. Thus, the screw drive 34 is rotated within sleeve 16 and driven forward or to the left in FIG. 1 causing sleeve 14 to telescope out of sleeve 16. The combined length of sleeves 14 and 16 thus increases. When the wire 38 cools there is no further torque applied to shell 36 by wire 38, and torsion spring 26 will rotate shell 36 back to its original angular position within drive unit 24. Grooves are cut into the screw threads to resist rotation of screw drive 34 in the opposite direction thereby insuring that ratchet 32 slips against the screw drive 34 when shell 3 is returned to its original angular orientation. Screw drive 34 remains in a new advanced longitudinal position within sleeve 16. In this manner rod 10 can be repeatedly incrementally lengthened by repeated heat cycling of motor 28. Rod 10 can only lengthen and the ratcheting action of ratchet 32 prevents it from shortening. The ratchet 32 is designed to release or disengage from screw drive 34 when a screw-driver or Allen wrench is placed into through-hex socket 50 of screw drive 34 during surgical placement and adjustment. Torsion spring 26 also provides some longitudinal compressive force which tends to urge ratchet 32 against screw drive 34, but placement of a tool through socket 50 allows ratchet 32 to be backed off and to disengage from screw 32. Withdrawal of the tool then allows spring 26 to urge ratchet 32 back into engagement with screw drive 34. The initial length of rod 10 can thus be manually adjusted up or down at the time of its initial surgical implantation.

The pick-up coil 30 receives energy from an external hand-held source of energy (not shown), such as a low frequency generator of electromagnetic radiation, which is brought into proximity with coil 30. Rod 10 is implanted beneath the skin barrier, while the source of energy is exterior to the body. The external inductive power source may be driven at conventional line frequency, in the event that the col 30 is be able to efficiently drive the muscle wire 38, then either a storage capacitor with a control diode can be added in circuit with coil 30, or with more complexity, a battery with a diode voltage multiplier, and control diode could be used. Any means of impedance matching between coil 30 and wire 38 on one hand and between coil 30 and the inductive power source on the other may be employed. The use of external power sources and inductively powered implanted coils is well known to the art and are routinely used, for example, in charging implanted pacemaker devices.

For a first alternative, energy would be fed into the pick-up coil until enough was stored in the capacitor to drive the motor 28. Upon the firing of the motor 28 the hand-held device would sense the discharge, and shut-off for the prescribed lock-out period.

The second alternative is the same, except that an onboard battery assists in charging the capacitor, and thus requires significantly more control electronics.

Figure 5:
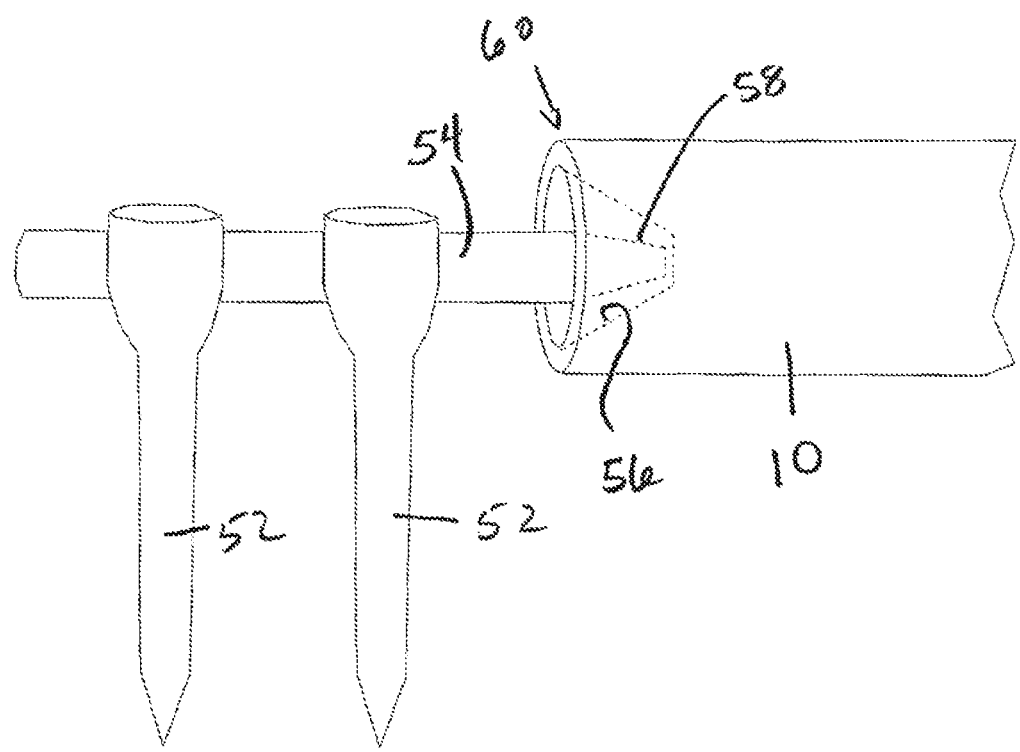
FIG. 5 is a side perspective view of a pair of pedicle screws showing a rotational coupling to the end of the rod of the invention.

Consider now the surgical implantation of rod 10 and its operation within the body. Two pedicle screws 52 as shown in FIG. 5 are placed at the top and two pedicle screws 52 at the bottom of the curve in a spine which being treated. Fixed head screws (not shown) are used. The expandable rod 10 is run above the fascia and beneath the skin between the two constructs. The rod 10 is then expanded daily typically for 2-3 months. The duration of treatment is variable and is determined according to medical considerations, which are not directly relevant here. After the desired curve in the spine is attained, the screws 52 and rod 10 are removed.

Figure 3:
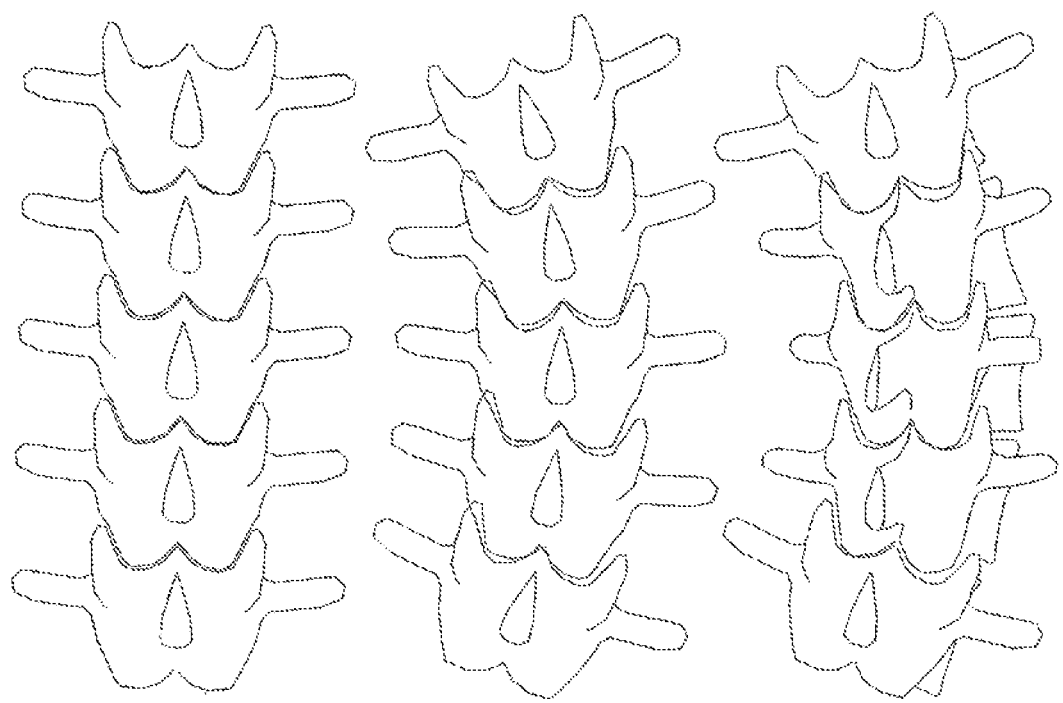
FIG. 3 is a posterior view, moving from the left to the right of the drawing, of a straight, lateral bending and scoliotic spine respectively.

FIG. 3 shows moving from left to right in the drawing a posterior view of a normal straight, normal in lateral bending, and a scoliotic spine. Note that with normal lateral bending as shown in the center there is no significant rotation. Indeed, in scoliosis as shown in the right most depiction as in lateral bending there is no significant increase in rotation. This is because scoliosis is caused by a tight ligamentum flavum. Because of this scoliosis patients have loss of kyphosis or are even lordotic, even in the thoracic spine. These facts can make a slight curve in the expanding rod 10 very useful as shown in the left most depiction in FIG. 4. As the spine straightens, rod 10 is also flexible enough to slowly straighten with the spine as shown in the right most depiction in FIG. 4.

Figure 4:
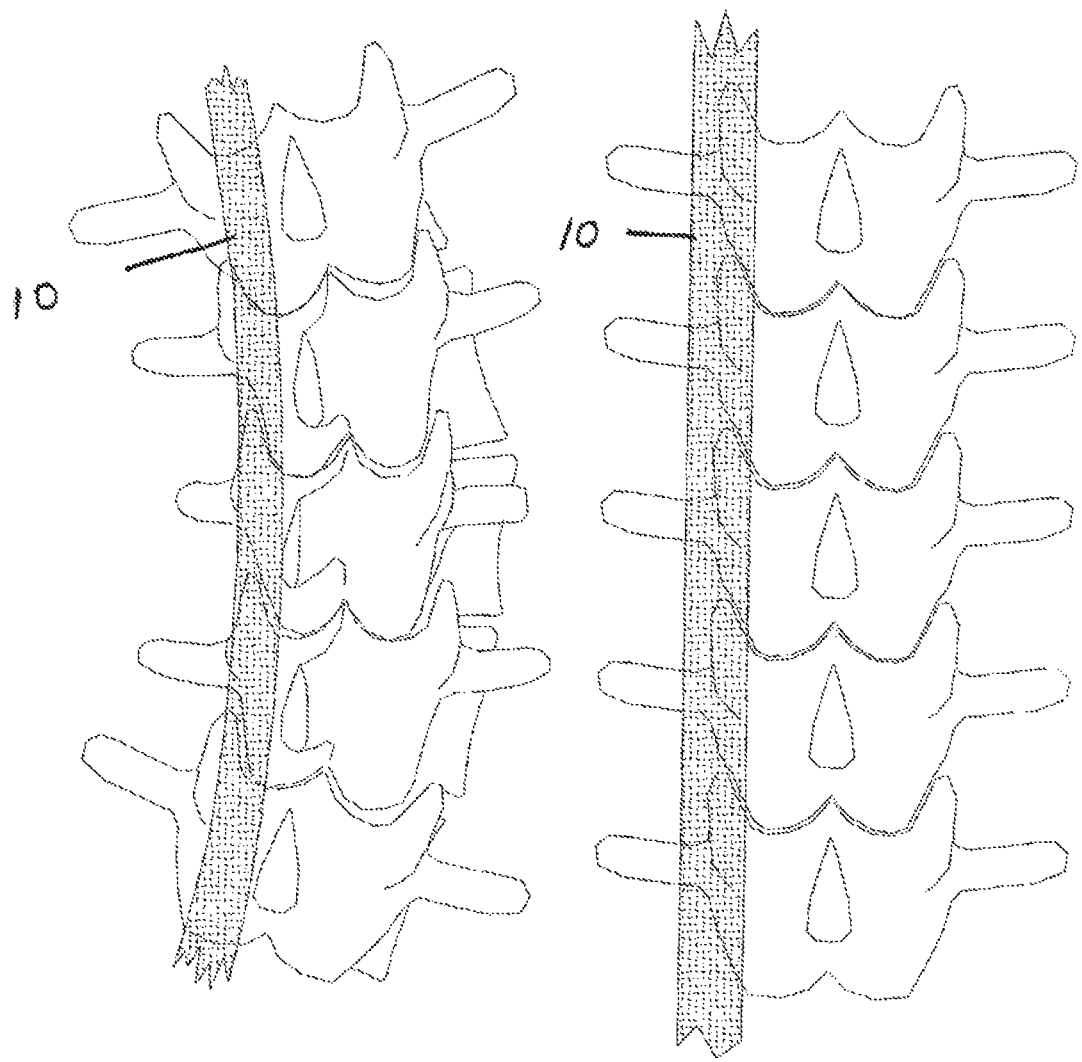
FIG. 4 is a posterior view of the rod of the invention as implanted next to a bent scoliotic spine in the left most depiction and next to a straightened spine in the right most depiction of the drawing.

FIG. 4 shows the initial rod placement in the left most drawing. As the rod 10 expands, the spine has nowhere to go except to have the pedicle screws 52 cut out or for the spine to straighten. Because the expansion is slow, the pedicle screws 52 don't cut out. As the spine straightens, and also because the rod 10 is posterior to the ligamentum flavum and is in a poor position to stretch the anterior longitudinal ligament, the spine will be pushed from a horizontal into a vertical position, thus restoring normal kyphosis.

In order to allow both rotation, and some play for the re-establishment of kyphosis, the rod-to-pedicle screw articulation is provided as shown in FIG. 5. Rod 10 is coupled to pedicle screws 52 by means of a pin 54 fixed to screws 52. The extend end 58 of pin 541 is tapered and is disposed into a conical socket 56 defined into the adjacent end 60 of rod 10. This allows rod 10 to swivel around the pivot provided between the socket-to-pin connection to rod 10 by fixed pin 54 and pedicle screws 52.

Scoliosis can be treated without difficult, conspicuous. (and ineffective) bracing; and without fusion. The key is to stretch out the ligamentum flavum. The proposed device discussed should be effective in stretching the spine out of scoliosis. This device would also have several applications other than the spine.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

For example, while a cycling rotational motor 28 with a rotary ratchet has been described, it is entirely within the scope of the invention that a cycled linear motor in combination with a linear ratcheting mechanism could be substituted to replace the illustrated embodiment.

Further, while an ohmically heated motor is the preferred embodiment, it is also possible to conceive of use of a thermally or otherwise powered piston motor where the driving fluid may be heated by RF diathermy or ultrasound energy.

Still further the motor may be a rotary motor or near motor with the propelling element of the motor is magnetically coupled to a moving magnetic field source and is combined through appropriate gearing to a ratcheting mechanism which telescopes rod 10.

Any means by which energy from an external source can be coupled into a motor which will mechanically telescope rod 10 is included within the spirit and scope of the invention.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

What is claimed is:

1. A method for correction of a scoliotic curve in a spine, the method comprising:
    implanting an expanding rod subcutaneously within a subject, the expanding rod including:
        a first end configured to be coupled to a first location on the subject's spine during implantation; and
        a second end configured to be coupled to a second location on the subject's spine during implantation,
        wherein the first end includes an inner member moveably coupled to and telescopically received by a hollow outer member of the second end,
        wherein the expanding rod includes a flexibility and is configured to be curved and aligned with a curve of the spine during implantation, and
    axially displacing the first end relative to the second end such that a force is applied to the scoliotic curve to modify the scoliotic curve,
    within the hollow outer member to move the drive mechanism toward the inner member such that a distance between an end of the drive mechanism and an end of the inner member decreases.

2. The method of claim 1, wherein the implanting of the expanding rod includes implanting the expanding rod posteriorly to the spine.

3. The method of claim 1, further comprising applying an externally controlled, incremental force to actuate the drive mechanism.

4. The method of claim 3, wherein the applying further comprises applying an external magnetic field to the drive mechanism to actuate the drive mechanism.

5. The method of claim 1, wherein the first end and the second end of the expanding rod share and are axially displaced along a common longitudinal axis.

6. The method of claim 1, wherein the drive mechanism includes a spring.

7. The method of claim 1, wherein the drive mechanism includes a wire.

8. The method of claim 7, wherein the wire is a nitinol wire.

9. The method of claim 1, wherein the drive mechanism includes a coil.

10. The method of claim 1, wherein the spine has a ligamentum flavum and wherein expansion of the expanding rod over an extended time period is configured to steadily stretch the ligamentum flavum of the spine, allowing the spine to straighten.

11. The method of claim 1, wherein the expanding rod includes an anti-rotation feature configured to prevent rotation of the inner member relative to the outer member.

12. A method for treating a spinal condition of a subject, the method including:
    modifying a state of the spinal condition by applying a force to an expandable rod implanted in the subject and coupled to first and second locations on a spine of the subject to cause a distance between a first end and a second end of the expandable rod to change,
    wherein the applying further includes applying the force to actuate a drive mechanism within a hollow outer member of the second end, thereby moving the drive mechanism toward an inner member of the first end, wherein the inner member of the first end is moveably coupled to the hollow outer member, such that a distance between an end of the drive mechanism and an end of the inner member decreases.

13. The method of claim 12, wherein the implanting of the expandable rod includes implanting the expandable rod posteriorly to the spine.

14. The method of claim 12, further comprising curving the expandable rod during the implanting.

15. The method of claim 14, further comprising aligning the curved expandable rod with a scoliotic curve of the spine.

16. The method of claim 15, wherein the modifying the state of the spinal condition includes modifying the scoliotic curve of the spine.

17. The method of claim 16, wherein the modifying the scoliotic curve of the spine includes stretching the scoliotic curve of the spine.

* * * * *